United States Patent [19]

Jones

[11] Patent Number: 5,220,926
[45] Date of Patent: Jun. 22, 1993

[54] FINGER MOUNTED CORE BIOPSY GUIDE

[76] Inventor: George T. Jones, 2112 W. Jefferson, Joliet, Ill. 60435

[21] Appl. No.: 912,247

[22] Filed: Jul. 13, 1992

[51] Int. Cl.⁵ ............................................ A61B 10/00
[52] U.S. Cl. .................................................. 128/754
[58] Field of Search .............. 128/749, 751, 753, 754; 606/167, 170

[56] References Cited

U.S. PATENT DOCUMENTS

| | | | |
|---|---|---|---|
| 3,595,217 | 7/1971 | Rheinfrank | 128/754 |
| 4,022,191 | 5/1977 | Jamshidi | |
| 4,340,066 | 7/1982 | Shah | 128/754 |
| 4,600,014 | 7/1986 | Beraha | 128/754 |
| 4,865,590 | 9/1989 | Marmar | 604/180 |
| 4,892,520 | 1/1990 | Gilbaugh | 604/117 |
| 4,991,592 | 2/1991 | Christ | 128/754 |
| 5,014,717 | 5/1991 | Lohrmann | 128/754 |

Primary Examiner—Max Hindenburg
Attorney, Agent, or Firm—Harpman & Harpman

[57] ABSTRACT

A core biopsy guide that is removably secured to the finger of a gloved hand to position a core biopsy needle sampling device adjacent the tissue of the organ to be sampled. The biopsy guide comprises an elongated tubular open-ended sleeve portion and a funnel portion in communication therewith. The biopsy guide provides a rigid path for a spring driven core biopsy needle device to be positioned therethrough engaging the target tissue to be biopsied.

3 Claims, 2 Drawing Sheets

FINGER MOUNTED CORE BIOPSY GUIDE

BACKGROUND OF THE INVENTION

1. Technical Field

This device relates to biopsy needle devices used to obtain sample specimens of cells and tissue to be analyzed by a pathologist and more particularly to biopsy needle guides used to position the biopsy needle for insertion into the tissue to be sampled.

There are two types of specimens which can be given to the pathologist for analysis, one type is the core of tissue i.e solid tissue and the other is a collection of cells or cytology.

For prostate biopsies, pathologist are much more attuned to working with a core rather than the cytological specimen since the average pathologist working in the field has a difficult time interpreting the cytology specimen. It is therefore imperative to obtain a good core tissue specimen for analysis purposes.

To obtain a cytological specimen, an aspiration biopsy is performed by attaching a hollow needle to a syringe. The needle is then guided to the biopsy cite, for example, in the prostate by digital manipulation by the surgeon. The needle introduced to a predetermined depth into the tissue and a vacuum is then created by withdrawing the syringe, therefore aspirating the cell material required. In this form of biopsy, the needle is moved back and forth rapidly dislodging cells which are sucked into the needle. The fluid then obtained is ejected from the needle by removing the syringe from the needle filling the syringe with air and re-attaching the syringe to the needle. The air is then used to force the cells onto a glass slide where a smear is made of the fluid obtained.

The core of tissue sampling method which is preferred and to which this device is designed for utilizes a needle mechanism consisting of an outer needle with a sharp stylet within. It is critical in this type of core sampling that the biopsy needle not be bent beyond certain parameters since it interferes with the mechanism which is required to rapidly advance the outer needle over the stylet, sampling the core within.

Accordingly, it is the object of this invention to provide a semi-rigid core biopsy needle guide which can be positioned on the finger of the surgeon and inserted into the body cavity for proper biopsy needle operation.

2. Description of Prior Art

Prior Art devices of this type have relied on a variety of different guide elements and structures that are used in combination and rely on the physician's gloved finger for insertion and positioning procedures, see for example U.S. Pat. Nos. 4,022,191, 4,865,590, 4,892,520 and U.S. Pat. No. 4,991,592.

In U.S. Pat. No. 4,022,191 a biopsy needle guard and guide is disclosed for use with an aspiration biopsy needle device. The guard and guide has a rigid tapered tubular element, a portion of which is segmented by longitudinally spaced circumferential grooves. Dependent on the desired depth of insertion required, the appropriate segmented portion can be removed shortening the overall guide. The aspiration needle is inserted in sealing relation into the guide for use.

U.S. Pat. No. 4,865,590 discloses a disposable prostate aspiration device which is adhesively attached to the gloved finger of the physician. The device consist of a guide tube secured to a band of flexible support material such as adhesive tape. The tube extends outwardly beyond the support material. The tube is "loaded" with an antibiotic compound and provides a flexible guide for the aspiration needle. Insertion of the aspiration biopsy needle displaces the antibiotic compound within.

A finger mounted surgical needle guide is set forth in U.S. Pat. No. 4,892,520. The needle guide has a center needle support with outwardly extending wings to mount and stabilize the guide on a surgeon's finger. A pliable touch sensitive ribbon/attaching web extends from the distal end of the guide and extends around the end of the surgeon's finger.

In U.S. Pat. No. 4,991,592 a tissue sampling device is disclosed having a finger receiving tubular member with a flexible needle guide positioned within. The needle guide extends outwardly beyond the tubular member and has a tapered open end within the tubular member. A biopsy needle assembly is guided within the needle guide for use.

SUMMARY OF THE INVENTION

A core biopsy needle guide positioned on the gloved finger of the physician to guide a core biopsy needle device to the target tissue of an organ.

The core biopsy guide defines a rigid pathway with a two-part guide structure having an open-ended tubular sleeve portion interconnected to a funnel portion that receives the core biopsy needle device. It is important to maintain a rigid pathway within the guide for proper functioning of the core biopsy needle device. Excessive bending of the core biopsy needle device will result in restricting its spring firing action resulting in diminished penetration into the target tissue and poor tissue core recovery.

DESCRIPTION OF THE PREFERRED EMBODIMENT

Figure 1:
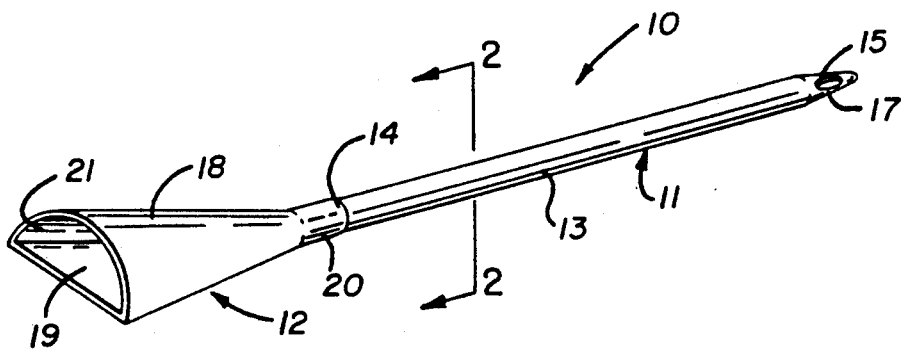
FIG. 1 is a perspective view of the biopsy needle guide.

Referring to FIG. 1 of the drawings, a core biopsy guide 10 can be seen having an elongated tubular sleeve portion 11 and a funnel portion 12. The tubular sleeve portion 11 is comprises of a tubular member 13 having oppositely disposed end openings at 14 and 15 defining an axial passageway 16 therebetween. The opening at 15 in the tubular member 13 is beveled forming an elongated ovaloid opening at 17 therein, best seen in FIGS. 1 and 5 of the drawings.

Figure 2:
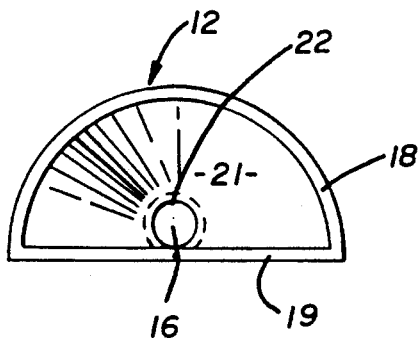
FIG. 2 is a section on lines 2—2 of FIG. 1.
Figure 3:
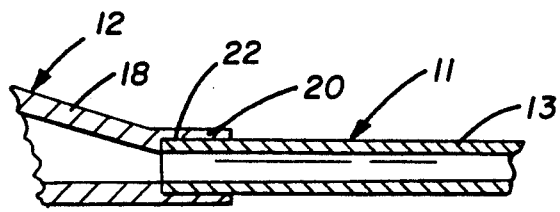
FIG. 3 is an enlarged portion of a cross-sectional view of the device.

The funnel portion 12 of the core biopsy guide 10 can be seen in FIGS. 1, 2, and 3 of the drawings having a generally transversely curved tapered thin walled upper surface 18 configuration extending from and integral with a relatively flat base portion 12 with an area of angular transition at 20 formed within. The funnel portion 12 defines a large opening at 21 of a known dimension and a receptacle opening at 22 of a dimension less than that of said opening 21.

The tubular member 13 is positioned is registering relationship within said reciprocal opening 22 as seen in FIG. 3 of the drawings. The funnel portion 12 is thus secured to the tubular member 13 within the area of angular transition defines a modified conical guide to direct a core biopsy needle assembly 23 into the axial passageway 16 of the tubular member 13 as hereinbefore described, best seen in FIG. 5 of the drawings.

In the preferred form of the invention, the diameter of the reciprocal opening at 22 is the same as that of the axial passageway 16 so that a smooth non-restrictive transition is achieved between the interior of the funnel portion 12 and the interior of the tubular member 13.

Figure 4:
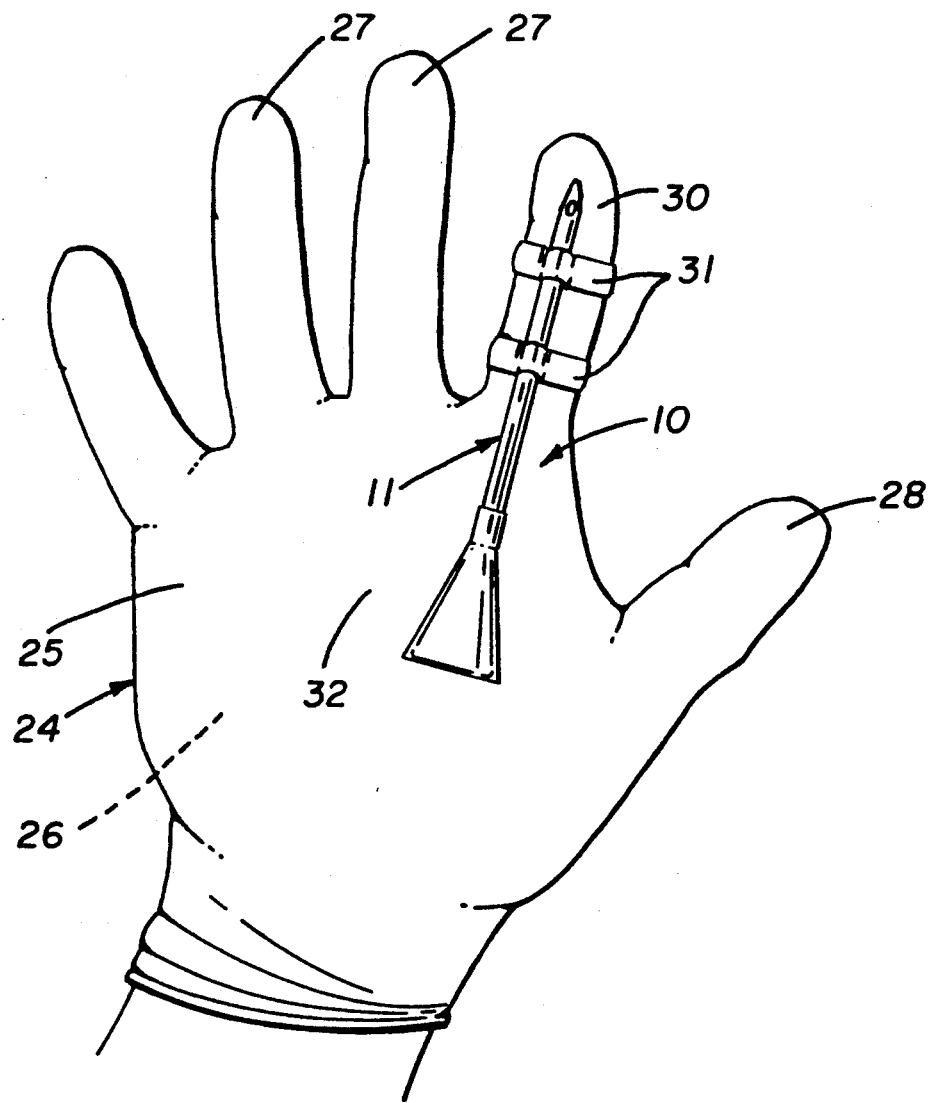
FIG. 4 is a plan view of the device embodying the positioning on the gloved hand ready for biopsy needle insertion.

Referring now to FIG. 4 of the drawings, the core biopsy guide 10 can be seen in use on a gloved hand 24 of a surgeon. A surgical rubber glove 25 is shown as will be well known to those skilled in the art which is comprised of a thin elastic material providing a non-porous barrier over a surgeon's hand 26. The gloved hand 24 has multiple finger portions 27, a palm area and a thumb position 28. The core biopsy guide 10 is removably secured to an index finger 30 by adhesive backed tape 31 or similar restrictive band elements.

The tubular sleeve portion 11 of the guide extends longitudinally along the index finger 30 and beyond to a palmar portion 32 of the gloved hand 24.

The funnel end portion 12 of the core biopsy guide 10 extends axially and longitudinally of the palmar portion 32 adjacent to the thumb portion 28 so that the core biopsy guide can be grasped by the respective thumb 28 and forefingers 27 of the surgeon's hand if and when required. In this preferred form of the invention, the base 19 of the funnel portion stabilizes the tubular member 13 against the surgeon's hand 24.

Figure 5:
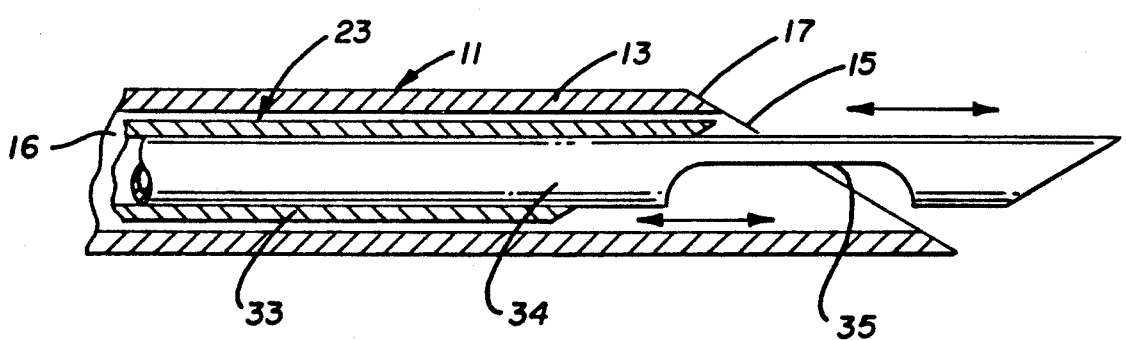
FIG. 5 is a cross-sectional view of the device with the outer needle and stylet.

Referring now to FIG. 5 of the drawings, the beveled end opening 15 of the core biopsy guide is illustrated with the biopsy needle assembly 23 within. The biopsy needle assembly 23 comprises an outer needle sleeve 33 and a sharp stylet 34 movably positioned within. The stylet 34 has a notch at 35 inwardly of its distal end. Once the core biopsy guide 10 has been positioned within the patient, the surgeon's index finger 30 adjacent the end of the guide is free to palpate a portion of the target tissue to be biopsied. The stylet 34 extends from the needle sleeve 33 deep into the target tissue (not shown) where the notch at 35 is filled with tissue.

The needle sleeve 33 is then advanced rapidly along the stylet 34 beyond the notch at 35 within the target tissue. The sharp needle sleeve 33 cuts the tissue leaving a core specimen within the notch at 35. The biopsy needle assembly 23 is then withdrawn through the core biopsy guide 10 which can remain within the patient if required for multiple core biopsy specimens.

Thus it will be seen that the core biopsy guide 10 has been illustrated and described and that it will be apparent to those skilled in the art that various modifications and changes may be made therein without departing from the spirit of the invention, therefore,

I claim:

1. A core biopsy guide for use in securing core biopsy sample tissues from a body organ in a body cavity by a biopsy needle assembly comprising in combination, a tubular sleeve portion and a funnel guide portion, said funnel guide portion having a tapered half arcuate surface configuration, an area of reduced diameter defining a receptacle opening at one end of said half arcuate surface configuration, said tubular sleeve portion comprising an elongated rigid tubular member, said tubular member having oppositely disposed open ends, one of said ends is registerable within said receptacle opening of said tubular funnel guide portion, said other of said open ends being beveled at its distal end, said tubular member having an axial passageway for guiding said biopsy needle therethrough into said body organ to be samples, said core biopsy guide is secured to a finger of a user for insertion into said body cavity with said core biopsy guide attached thereto.

2. The core biopsy guide of claim 1 wherein said receptacle opening within said half-arcuate surface configuration has an area of angular transition of a known internal dimension equal to that of said tubular members axial passageway.

3. The core biopsy guide of claim 1 wherein said biopsy needle comprises an outer needle sleeve, a notched stylet movably positioned within, said biopsy needle is receivably guided within said core biopsy needle guide within said body cavity of the patient.

* * * * *